(12) United States Patent
Kutsuna et al.

(10) Patent No.: US 11,287,500 B2
(45) Date of Patent: Mar. 29, 2022

(54) MAGNETIC RESONANCE IMAGING APPARATUS AND MAGNETIC RESONANCE IMAGING METHOD

(71) Applicant: CANON MEDICAL SYSTEMS CORPORATION, Otawara (JP)

(72) Inventors: Hideaki Kutsuna, Kawasaki (JP); Hidenori Takeshima, Kawasaki (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 0 days.

(21) Appl. No.: 17/064,779

(22) Filed: Oct. 7, 2020

(65) Prior Publication Data

US 2021/0103020 A1    Apr. 8, 2021

(30) Foreign Application Priority Data

Oct. 8, 2019 (JP) .............................. JP2019-184912

(51) Int. Cl.
*G01R 33/48* (2006.01)
*G01R 33/54* (2006.01)
*G01R 33/56* (2006.01)

(52) U.S. Cl.
CPC ....... *G01R 33/4824* (2013.01); *G01R 33/543* (2013.01); *G01R 33/5608* (2013.01)

(58) Field of Classification Search
USPC ........................................................ 324/309
See application file for complete search history.

(56) References Cited

U.S. PATENT DOCUMENTS

| 5,349,294 | A  | * | 9/1994  | Kasuboski | G01R 33/446 |
|           |    |   |         |           | 324/309     |
| 9,921,285 | B2 |   | 3/2018  | Otazo et al. | |
| 10,386,437| B2 |   | 8/2019  | Wundrak et al. | |
| 2003/0117136 | A1 | * | 6/2003 | Wang | G01R 33/5676 |
|           |    |   |         |           | 324/306     |
| 2012/0146641 | A1 | * | 6/2012 | Wu | G01R 33/4826 |
|           |    |   |         |           | 324/309     |
| 2017/0307711 | A1 |   | 10/2017 | Wundrak et al. | |
| 2018/0372824 | A1 |   | 12/2018 | Saito et al. | |

(Continued)

FOREIGN PATENT DOCUMENTS

| EP | 2 550 541 A1 | 1/2013 |
| EP | 2 550 541 B1 | 7/2017 |
| EP | 3 470 869 A1 | 4/2019 |

(Continued)

OTHER PUBLICATIONS

Extended European Search Report dated Mar. 3, 2021 in European Patent Application No. 20200417.2, 12 pages.

(Continued)

*Primary Examiner* — Rodney E Fuller
(74) *Attorney, Agent, or Firm* — Oblon, McClelland, Maier & Neustadt, L.L.P.

(57) ABSTRACT

A magnetic resonance imaging apparatus according to an embodiment includes processing circuitry. The processing circuitry is configured to set a rotation angle of a non-Cartesian trajectory in a k-space on the basis of information related to cyclic movements of a subject to be imaged, to obtain k-space data by rotating the non-Cartesian trajectory at the set rotation angle, and to generate an image by reconstructing the k-space data.

14 Claims, 7 Drawing Sheets

(56) References Cited

U.S. PATENT DOCUMENTS

2020/0278413 A1    9/2020   Kutsuna et al.
2020/0300952 A1*   9/2020   Doneva ............... G01R 33/567

FOREIGN PATENT DOCUMENTS

| JP | 2017-529953 A | 10/2017 |
| JP | 2019-005289 A | 1/2019 |
| JP | 2020-137923 A | 9/2020 |
| JP | 2021-87669 A  | 6/2021 |

OTHER PUBLICATIONS

Keigo Kawaji et al., "Whole Heart Coronary Imaging with Flexible Acquisition Window and Trigger Delay" PLOS One, vol. 10, No. 2, XP055777089, Feb. 26, 2015, p. 1-14.

Winkelmann et al., "An Optimal Radial Profile Order Base on the Golden Ratio for Time-Resolved MRI", IEEE Transactions on Medical Imaging, vol. 26, No. 1, 2007, pp. 68-76.

* cited by examiner

MAGNETIC RESONANCE IMAGING APPARATUS AND MAGNETIC RESONANCE IMAGING METHOD

CROSS-REFERENCE TO RELATED APPLICATIONS

This application is based upon and claims the benefit of priority from Japanese Patent Application No. 2019-184912 filed on Oct. 8, 2019; the entire contents of which are incorporated herein by reference.

FIELD

Embodiments described herein relate generally to a magnetic resonance imaging apparatus and a magnetic resonance imaging method.

BACKGROUND

When magnetic resonance imaging is implemented by using a radial-type acquisition sequence, a method is known by which acquisitions are performed using a plurality of spokes going through the origin of a k-space, so that rotation angles are mutually different by a golden angle GA (approximately)111.25°. By using this acquisition method, it is possible to obtain k-space data having excellent dispersiveness.

In actual imaging situations, however, cyclic movements such as respiration and heartbeats, for example, are present. Thus, when those cyclic movements and the imaging cycles synchronize with each other, image quality may be degraded in some situations.

DETAILED DESCRIPTION

A magnetic resonance imaging apparatus according to at least one aspect of the present disclosure includes processing circuitry. The processing circuitry is configured to set a rotation angle of a non-Cartesian trajectory in a k-space on the basis of information related to cyclic movements of a subject to be imaged (or biological information), to obtain k-space data by rotating the non-Cartesian trajectory at the set rotation angle, and to generate an image by reconstructing the k-space data.

Exemplary embodiments of the present disclosure will be explained below, with reference to the accompanying drawings. Some of the constituent elements that are the same as one another will be referred to by using the same reference characters, and duplicate explanations thereof will be omitted.

First Embodiment

Figure 1:
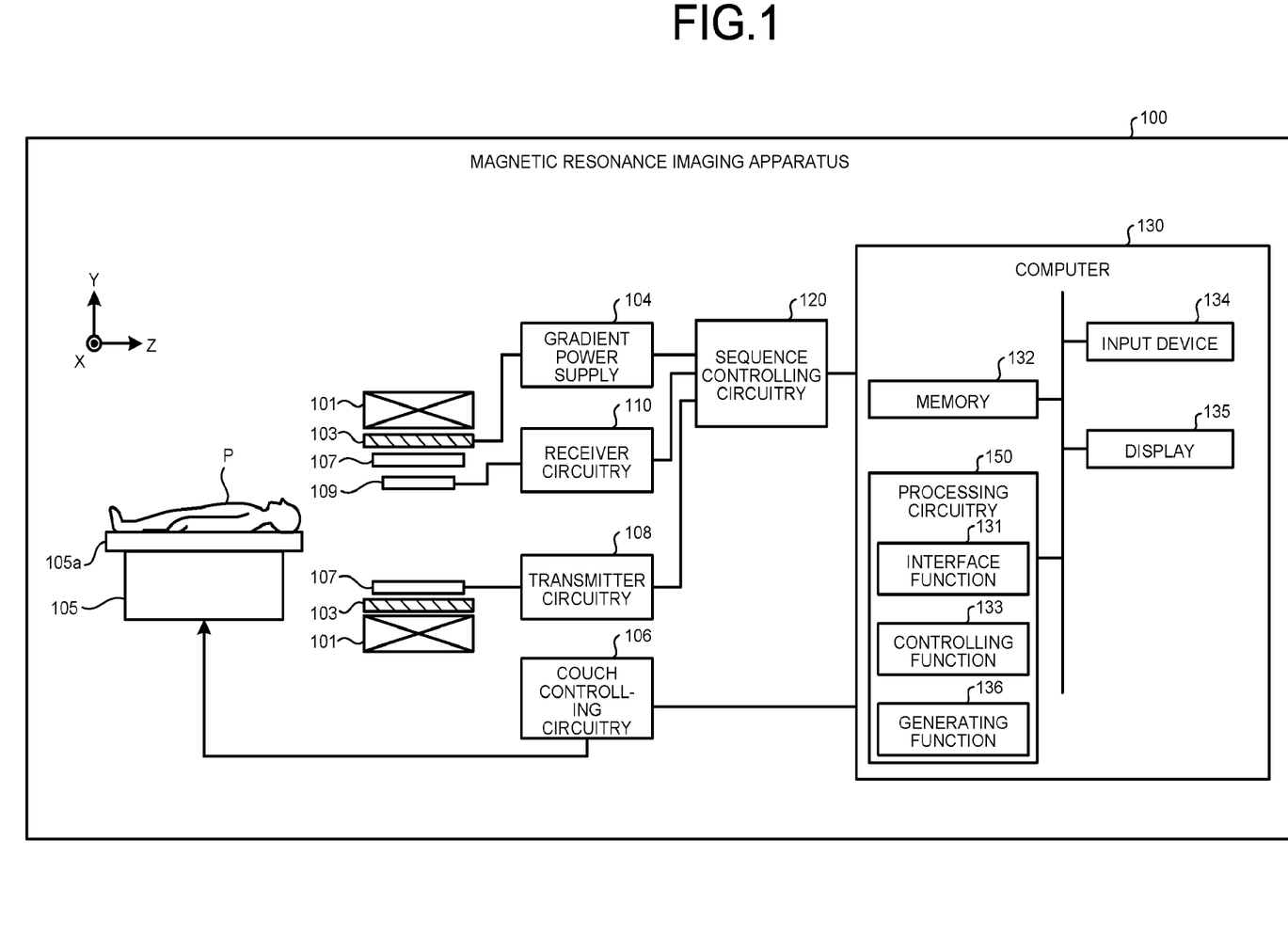
FIG. 1 is a diagram illustrating a magnetic resonance imaging apparatus according to an embodiment.

FIG. 1 is a block diagram illustrating a magnetic resonance imaging apparatus 100 according to a first embodiment. As illustrated in FIG. 1, the magnetic resonance imaging apparatus 100 includes a static magnetic field magnet 101, a static magnetic field power supply (not illustrated), a gradient coil 103, a gradient power supply 104, a couch 105, couch controlling circuitry 106, a transmitter coil 107, transmitter circuitry 108, a receiver coil 109, receiver circuitry 110, and sequence controlling circuitry 120 (a sequence controlling unit), and a computer 130 (which may be referred to as an "image processing apparatus"). The magnetic resonance imaging apparatus 100 does not include a subject P (e.g., a human body). Further, the configuration illustrated in FIG. 1 is merely an example. For instance, any of the functional units in the sequence controlling circuitry 120 and the computer 130 may be integrated together or configured separately as appropriate.

The static magnetic field magnet 101 is a magnet formed to have a hollow and substantially circular cylindrical shape and is configured to generate a static magnetic field in the space inside thereof. For example, the static magnetic field magnet 101 is a superconductive magnet or the like. Alternatively, the static magnetic field magnet 101 may be a permanent magnet.

The gradient coil 103 is a coil formed to have a hollow and substantially circular cylindrical shape and is arranged on the inside of the static magnetic field magnet 101. The gradient coil 103 is formed by combining together three coils corresponding to X-, Y-, and Z-axes that are orthogonal to one another. The three coils are configured to individually receive supply of an electric current from the gradient power supply 104 and to generate gradient magnetic fields of which the magnetic field intensities vary along the X-, Y-, and Z-axes. The gradient magnetic fields generated along the X-, Y-, and Z-axes by the gradient coil 103 are, for example, a slice gradient magnetic field Gs, a phase-encoding gradient magnetic field Ge, and a read-out gradient magnetic field Gr. The gradient power supply 104 is configured to supply the electric current to the gradient coil 103.

The couch 105 includes a couchtop 105a on which the subject P is placed. Under control of the couch controlling circuitry 106, the couchtop 105a is inserted to the inside of the hollow space (an image taking opening) of the gradient coil 103 while the subject P is placed thereon. Normally, the couch 105 is installed in such a manner that the longitudinal direction thereof extends parallel to the central axis of the static magnetic field magnet 101. Under control of the computer 130, the couch controlling circuitry 106 is configured to drive the couch 105 so as to move the couchtop 105a in longitudinal directions and up-and-down directions.

The transmitter coil 107 is arranged on the inside of the gradient coil 103 and is configured to generate a radio frequency magnetic field by receiving supply of a Radio Frequency (RF) pulse from the transmitter circuitry 108. The transmitter circuitry 108 is configured to supply the transmitter coil 107 with the RF pulse corresponding to a Larmor frequency determined by the type of a target atom and the magnetic field intensities.

The receiver coil 109 is arranged on the inside of the gradient coil 103 and is configured to receive a magnetic resonance signal (which hereinafter may be referred to as "MR signal" as necessary) emitted from the subject P due to an influence of the radio frequency magnetic field. When having received the magnetic resonance signal, the receiver coil 109 is configured to output the received magnetic resonance signal to the receiver circuitry 110.

The transmitter coil 107 and the receiver coil 109 described above are merely examples. It is possible to use one or a combination of two or more, from among the following: a coil having only a transmitting function; a coil having only a receiving function; and a coil having transmitting and receiving functions.

The receiver circuitry 110 is configured to detect the magnetic resonance signal output from the receiver coil 109 and to generate magnetic resonance data on the basis of the detected magnetic resonance signal. More specifically, the receiver circuitry 110 is configured to generate the magnetic resonance data by performing a digital conversion on the magnetic resonance signal output from the receiver coil 109. Further, the receiver circuitry 110 is configured to transmit the generated magnetic resonance data to the sequence controlling circuitry 120. Alternatively, the receiver circuitry 110 may be provided on the side of a gantry device including the static magnetic field magnet 101, the gradient coil 103, and the like. Furthermore, the receiver coil 109 may be provided with a part of the functions of the receiver circuitry 110 such as, for example, the function to perform the digital conversion on the magnetic resonance signal.

The sequence controlling circuitry 120 is configured to perform an image taking process on the subject P, by driving the gradient power supply 104, the transmitter circuitry 108, and the receiver circuitry 110, on the basis of sequence information transmitted thereto from the computer 130. In this situation, the sequence information is information defining a procedure for performing the image taking process. The sequence information defines: the intensity of the electric current to be supplied by the gradient power supply 104 to the gradient coil 103 and the timing with which the electric current is to be supplied; the intensity of the RF pulse to be supplied by the transmitter circuitry 108 to the transmitter coil 107 and the timing with which the RF pulse is to be applied; the timing with which the magnetic resonance signal is to be detected by the receiver circuitry 110, and the like. For example, the sequence controlling circuitry 120 may be an integrated circuit such as an Application Specific Integrated Circuit (ASIC) or a Field Programmable Gate Array (FPGA), or an electronic circuit such as a Central Processing Unit (CPU) or a Micro Processing Unit (MPU). Details of pulse sequences executed by the sequence controlling circuitry 120 will be explained later.

Further, when having received the magnetic resonance data from the receiver circuitry 110 as a result of performing the image taking process on the subject P by driving the gradient power supply 104, the transmitter circuitry 108, and the receiver circuitry 110, the sequence controlling circuitry 120 transfers the received magnetic resonance data to the computer 130.

The computer 130 is configured to exercise overall control of the magnetic resonance imaging apparatus 100, generation of images, and the like. The computer 130 includes a memory 132, an input device 134, a display 135, and processing circuitry 150. The processing circuitry 150 includes an interface function 131, a controlling function 133, and a generating function 136.

In the first embodiment, processing functions performed by the interface function 131, the controlling function 133, and the generating function 136 are stored in the memory 132 in the form of computer-executable programs. The processing circuitry 150 is a processor configured to realize the functions corresponding to the programs, by reading and executing the programs from the memory 132. In other words, the processing circuitry 150 that has read the programs has the functions illustrated within the processing circuitry 150 in FIG. 1. With reference to FIG. 1, the example is explained in which the single processing circuitry (i.e., the processing circuitry 150) realizes the processing functions implemented by the interface function 131, the controlling function 133, and the generating function 136; however, another arrangement is also acceptable in which the processing circuitry 150 is structured by combining together a plurality of independent processors, so that the functions are realized as a result of the processors executing the programs. In other words, each of the functions described above may be configured as a program, so that the single processing circuitry (i.e., the processing circuitry 150) executes the programs. In another example, one or more specific functions may be installed in a dedicated independent program-executing circuit. Further, in FIG. 1, the interface function 131, the controlling function 133, and the generating function 136 are examples of a receiving unit, a controlling unit, and a generating unit, respectively. Further, the sequence controlling circuitry 120 is an example of a sequence controlling unit.

The term "processor" used in the above explanations denotes, for example, a Central Processing Unit (CPU), a Graphical Processing Unit (GPU), or a circuit such as an Application Specific Integrated Circuit (ASIC) or a programmable logic device (e.g., a Simple Programmable Logic Device [SPLD], a Complex Programmable Logic Device [CPLD], or a Field Programmable Gate Array [FPGA]). The one or more processors realize the functions by reading and executing the programs saved in the memory 132.

Alternatively, instead of saving the programs in the memory 132, it is also acceptable to directly incorporate the programs in the circuits of the one or more processors. In that situation, the one or more processors realize the functions by reading and executing the programs incorporated in the circuits thereof. Similarly, the couch controlling circuitry 106, the transmitter circuitry 108, the receiver circuitry 110, and the like are also structured by using one or more electronic circuits such as the processors described above.

By employing the interface function 131, the processing circuitry 150 is configured to transmit the sequence information to the sequence controlling circuitry 120 and to receive the magnetic resonance data from the sequence controlling circuitry 120. Further, when having received the magnetic resonance data, the processing circuitry 150 including the interface function 131 is configured to store the received magnetic resonance data into the memory 132.

The magnetic resonance data stored in the memory 132 is arranged into a k-space by the controlling function 133. As a result, the memory 132 stores k-space data therein.

The memory 132 is configured to store therein the magnetic resonance data received by the processing circuitry 150 including the interface function 131, the k-space data arranged in the k-space by the processing circuitry 150 including the controlling function 133, image data generated by the processing circuitry 150 including the generating function 136, and the like. For example, the memory 132 is a semiconductor memory element such as a Random Access Memory (RAM) or a flash memory, or a hard disk, an optical disk, or the like.

The input device 134 is configured to receive various types of instructions and inputs of information from an operator. For example, the input device 134 may be a pointing device such as a mouse or a trackball, may be a selecting device such as a mode changing switch, or may be an inputting device such as a keyboard. Under control of the processing circuitry 150 including the controlling function 133, the display 135 is configured to display a Graphical User Interface (GUI) used for receiving an input of an image taking condition, an image generated by the processing circuitry 150 including the generating function 136, and the like. The display 135 is, for example, a display such as a liquid crystal display.

By employing the controlling function 133, the processing circuitry 150 is configured to exercise overall control of the magnetic resonance imaging apparatus 100 and to control image taking processes, image generating processes, image display processes, and the like. For example, the processing circuitry 150 including the controlling function 133 is configured to receive the input of the image taking condition (an image taking parameter or the like) through the GUI and to generate the sequence information according to the received image taking condition. Further, the processing circuitry 150 including the controlling function 133 is configured to transmit the generated sequence information to the sequence controlling circuitry 120.

By employing the generating function 136, the processing circuitry 150 is configured to generate an image by reading the k-space data from the memory 132 and performing a reconstruction process such as a Fourier transform on the read k-space data.

Next, a background of the embodiment will briefly be explained.

When magnetic resonance imaging is implemented by using a radial-type acquisition sequence, a method is known by which acquisitions are performed using a plurality of spokes going through the origin of a k-space, so that rotation angles are mutually different by a golden angle GA (approximately)111.25° or an angle derived from the golden angle GA such as 180°−GA, 360°−2×GA, or 2×GA. By using this acquisition method, the intervals between the spokes filling the k-space are kept to three types or less even in the worst situation. As a result, it is possible to evenly acquire the k-space data in all the directions in the k-space. In other words, it is possible to obtain k-space data having excellent dispersiveness. Further, these acquisitions have an advantage where it is possible to acquire k-space data having excellent dispersiveness no matter at which time a section of the data currently being taken is extracted, because the spokes rotate at a constant angle at any time.

However, when magnetic resonance imaging is implemented while varying the rotation angle of the spokes by the golden angle GA, because the golden angle GA is a fixed angle, there is a limitation to the degree of freedom of the imaging process. In other words, there may be some situations where it is impossible to obtain high-quality images simply by using a fixed spoke rotation angle such as the golden angle GA or one selected from among certain angles derived from the golden angle GA such as 180°−GA, 360°−2×GA, and 2×GA. For example, in actual imaging situations, cyclic movements such as respiration and heartbeats are present. Thus, when those cyclic movements and the imaging cycles synchronize with each other, image quality may be degraded in some situations. In other words, depending on the cycles of the movements such as the respiration, the heartbeats, or the like, it may be impossible, in some situations, to sufficiently guarantee the dispersiveness of the k-space data even when the imaging processes are set with a rotation angle using the golden angle GA.

Figure 2:
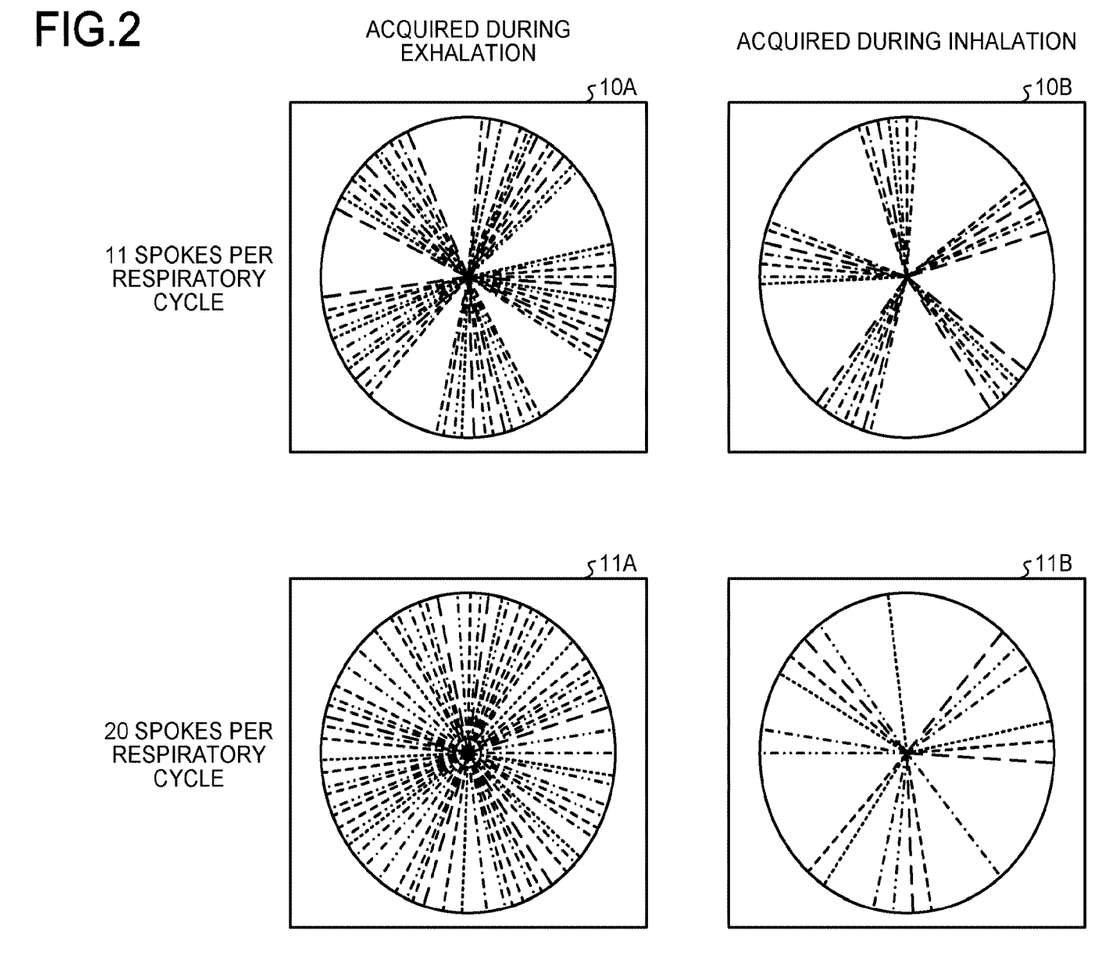
FIG. 2 is a drawing for explaining a background of the embodiment.

FIG. 2 is a drawing for explaining an example of the dispersiveness of the k-space data. In FIG. 2, an acquisition 10A is illustrated with an example of k-space data acquired during exhalation, in an example in which the sequence controlling circuitry 120 acquires k-space data corresponding to 11 spokes per respiratory cycle. In contrast, an acquisition 10B is illustrated with an example of k-space data acquired during inhalation, in an example in which the sequence controlling circuitry 120 acquires k-space data corresponding to 11 spokes per respiratory cycle. Further, an acquisition 11A is illustrated with an example of k-space data acquired during exhalation, in an example in which the sequence controlling circuitry 120 acquires k-space data corresponding to 20 spokes per respiratory cycle. In contrast, an acquisition 11B is illustrated with an example of k-space data acquired during inhalation, in an example in which the sequence controlling circuitry 120 acquires k-space data corresponding to 20 spokes per respiratory cycle. In FIG. 2, each of the dotted lines represents a different one of the spokes subject to the acquisitions.

As illustrated in FIG. 2, when the acquisitions corresponding to 11 spokes are performed per respiratory cycle, the positions subject to the acquisitions in the k-space are biased toward a specific direction in the k-space, when the inhalation period only or the exhalation period only is taken into consideration. Further, when the acquisitions corresponding to 20 spokes are performed per respiratory cycle, although the situation is improved compared to the example with the acquisitions corresponding to 11 spokes per respiratory cycle, the positions subject to the acquisitions in the k-space are still biased toward a specific direction in the k-space, when the inhalation period only or the exhalation period only is taken into consideration. In this situation, when imaging processes are performed throughout one respiratory cycle, the acquired images are supposed to be such images obtained by combining an image acquired from the k-space data during the exhalation with another image acquired from the k-space data during the inhalation. However, between the inhalation period and the exhalation period, the position of the imaged subject may be different due to movements and the like. Accordingly, when the dispersiveness of the k-space is not satisfactory because the positions subject to the acquisitions in the k-space are biased toward a specific direction in the k-space while the inhalation period only or the exhalation period only is taken into consideration, there is a possibility that the image quality may be degraded.

As explained above, when cyclic movements such as respiration are present, there is a possibility that the image quality may be degraded even with the radial-type sampling using the golden angle GA, when the relationship between the cycle of the movements such as the respiration and the cycle of the imaging is also taken into consideration. However, because the sampling using the golden angle GA has the advantage where the k-space data exhibits high dispersiveness, it is worthwhile to utilize this sampling method.

On the basis of the background described above, according to a magnetic resonance imaging method in an embodiment, the processing circuitry 150 is configured, by employing the controlling function 133, to select one of a plurality of acquisition patterns having mutually-different rotation angles of the spokes, in a non-Cartesian coordinate system. The sequence controlling circuitry 120 is configured to acquire k-space data by executing a pulse sequence by using the selected acquisition pattern, whereas the processing circuitry 150 is configured, by employing the generating function 136, to generate an image by reconstructing the k-space data. In this situation, the processing circuitry 150 is configured, by employing the controlling function 133, to set a spoke rotation angle for trajectories in the acquisition pattern, on the basis of the expression presented below obtained by generalizing the golden angle. The spoke rotation angle defined in the expression below will hereinafter be referred to as a "platinum angle (PA)" for the sake of convenience.

$$PA(N) = \frac{180°}{(N+1/\varphi)}, \varphi = \frac{1+\sqrt{5}}{2} \approx 1.618 \quad (1)$$

In Mathematical Expression (1), N denotes a natural number, while PA(N) denotes a platinum angle corresponding to N, and φ is a constant based on a golden ratio. In this situation, when N=1, PA(N) is equal to approximately 111.25°, which is the abovementioned golden angle. Accordingly, the platinum angle is considered as a generalized golden angle. For this reason, by performing radial sampling using the platinum angle, the sequence controlling circuitry 120 is able to maintain high dispersiveness of the k-space data, similarly to the radial sampling using the golden angle. Further, unlike the golden angle, the platinum angle has a degree of freedom regarding the parameter N. Accordingly, as a result of the processing circuitry 150 appropriately selecting the parameter N, the sequence controlling circuitry 120 is able to execute an appropriate pulse sequence corresponding to biological information of each subject, and the image quality is thus enhanced.

This configuration will be explained, with reference to FIG. 3 and FIGS. 4A to 4C.

Figure 3:
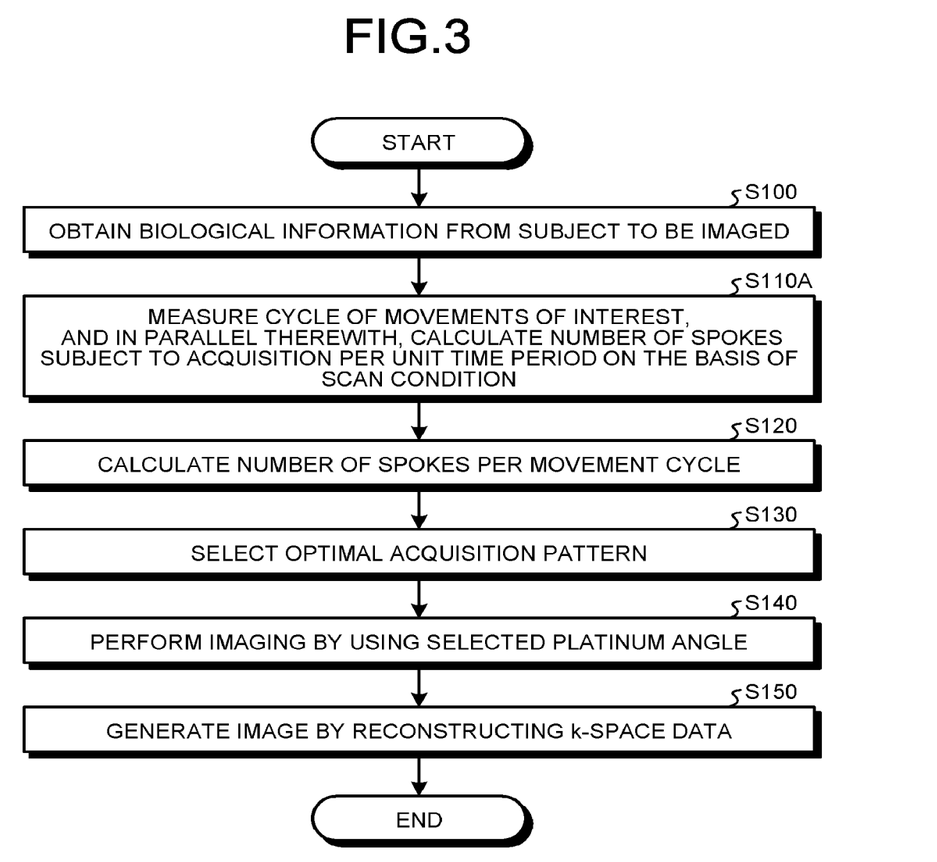
FIG. 3 is a flowchart illustrating a processing procedure performed by a magnetic resonance imaging apparatus according to a first embodiment.

FIG. 3 is a flowchart illustrating a processing procedure performed by the magnetic resonance imaging apparatus according to the first embodiment.

To begin with, at step S100, by employing the controlling function 133, the processing circuitry 150 obtains biological information such as information about respiration or information about heartbeats from the subject to be imaged, via a biological information obtaining device such as a respiratory information acquiring device or an electrocardiograph, for example. Possible embodiments are not limited to the example in which these pieces of biological information are obtained from a biological information obtaining device. These pieces of biological information may be obtained from an input by a user.

Subsequently, at step S110A, by employing the controlling function 133, the processing circuitry 150 measures a cycle of the movements of interest, and in parallel therewith, calculates the number of spokes subject to the acquisitions per unit time period from a scan condition. For example, by employing the controlling function 133, the processing circuitry 150 measures a respiratory cycle serving as the cycle of the movements of interest, as "4 seconds", on the basis of the information about respiration, which is the biological information of the subject to be imaged obtained at step S100. In parallel therewith, by employing the controlling function 133, the processing circuitry 150 obtains the scan condition from the sequence controlling circuitry 120 and calculates the number of spokes subject to the acquisitions per second as "4.0", for example.

After that, at step S120, by employing the controlling function 133, the processing circuitry 150 calculates the number of spokes per movement cycle. For example, when the respiratory cycle, which is the cycle of the movements of interest, is "4 second", whereas the number of spokes subject to the acquisitions per second is "4.0", the processing circuitry 150 calculates, by employing the controlling function 133, the number of spokes per movement cycle, i.e., the number of spokes per respiratory cycle, as 4.0× 4=16.0.

Subsequently, at step S130, by employing the controlling function 133, the processing circuitry 150 references a plurality of acquisition patterns having mutually-different rotation angles and corresponding to a plurality of trajectories having mutually-different rotation angles and further selects an appropriate acquisition pattern from among the referenced acquisition patterns. In one example, by employing the controlling function 133, the processing circuitry 150 references, as the plurality of acquisition patterns, a plurality of platinum angle sampling patterns having mutually-different platinum angles PA(N) serving as rotation angles and selects a sampling pattern having an optimal platinum angle PA(N) from among the referenced acquisition patterns, in accordance with a distribution of k-space data to be arranged. In other words, from among the plurality of acquisition patterns having the mutually-different settings for the rotation angles of the trajectories, the processing circuitry 150 selects the acquisition pattern in accordance with the distribution of the k-space data to be used to generate the image. In one example, by employing the controlling function 133, the processing circuitry 150 selects an optimal acquisition pattern by selecting an optimal N on the basis of an index (a dispersion index value) indicating dispersiveness of the k-space, in the situation where data in a specific temporal phase such as during exhalation is extracted, for example, from among the plurality of acquisition patterns having the mutually-different platinum angles PA(N). In other words, the processing circuitry 150 is configured to select the acquisition pattern having high dispersiveness of the k-space, from among the plurality of acquisition patterns.

In the present example, the index (the dispersion index value) indicating the dispersiveness of the k-space is, for example, a ratio of $SNR_{GOLDENRATIO}$ to $SNR_{uniform}$, where $SNR_{GOLDENRATIO}$ is a Signal to Noise Ratio (SNR) corresponding to sampling performed with the golden angle or the platinum angle, whereas SNR uniform is an SNR corresponding to sampling performed while the intervals between spokes that are adjacently arranged in the k-space are regular. It is possible to calculate the index by using the following expression:

$$\frac{SNR_{GOLDENRATIO}}{SNR_{UNIFORM}} = \sqrt{\frac{\frac{\pi^2}{P}}{\Sigma_{i=0}^{P-1}(\Delta\varphi_i)^2}} \quad (2)$$

In Mathematical Expression (2), P denotes the number of spokes subject to the data acquisitions, whereas $\Delta\varphi i$ denotes the angle difference between an i-th spoke and an (i+1)th spoke, when the spokes subject to the acquisitions in the sampling with the golden angle (the platinum angle) are sorted according to the magnitudes of the angles formed with an initial line serving as a reference.

It is expected that the closer the spokes arranged in the k-space are to the state of being arranged at regular intervals in the k-space, the larger is the dispersion index value described above. The larger the dispersion index value is, the more desirable. The smaller the variance value is of the angles formed by adjacently-positioned spokes that are arranged in the k-space with the sampling using the golden angle (the platinum angle), the larger is the dispersion index value.

Next, comparison examples on the assumption that the number of spokes per one breath is 18 will be explained with reference to FIGS. 4A, 4B, and 4C. Because the respiratory cycle is not necessarily always stable, the value of N that maximizes an average of dispersion index values in the range of 18±2 spokes, for example, shall be selected as an optimal N.

Figure 4A:
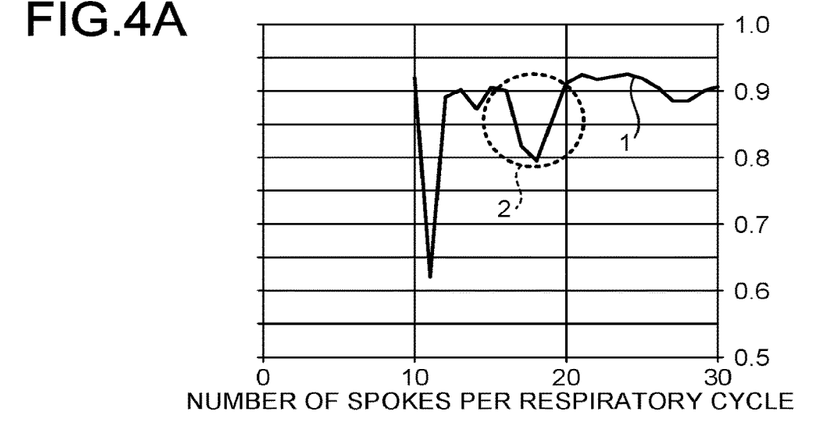
FIG. 4A is a chart for explaining a magnetic resonance imaging method according to a comparison example.

In FIG. 4A, chart 1 is obtained as a comparison example by plotting values of the dispersion index value when the golden angle sampling is performed in the exhalation period temporal phase in one respiratory cycle, as a mathematical function of the number of spokes per respiratory cycle. When the data from a specific temporal phase such as the exhalation time period in one respiratory cycle is extracted, the dispersion index value exhibits a decreasing tendency in region 2 where the number of spokes per respiratory cycle is in the range of 16 to 20. In other words, in region 2, the distribution of the spokes arranged in the k-space is biased, and the image quality is expected to be degraded. Accordingly, by employing the controlling function 133, the processing circuitry 150 selects, as an optimal N, the value of N that maximizes the dispersion index value when the sampling is performed with the platinum angle PA(N), while varying N with respect to "the number of spokes per movement cycle" calculated at step S120.

Figure 4B:
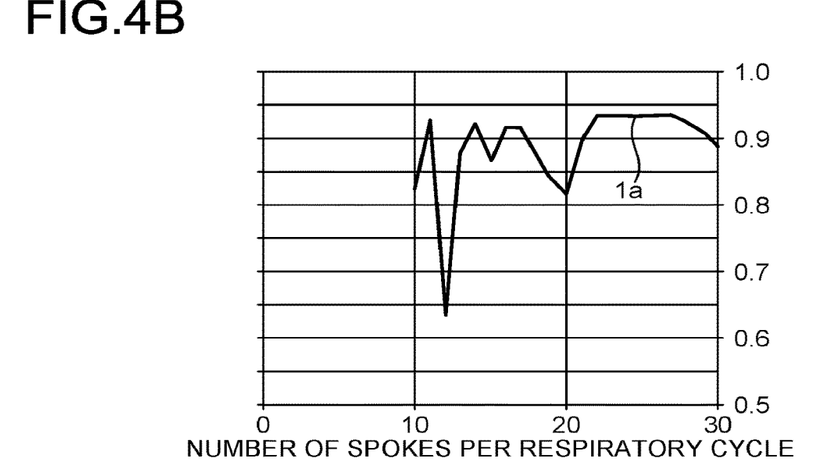
FIG. 4B is a chart for explaining a magnetic resonance imaging method according to the first embodiment.

In FIG. 4B, chart 1a is obtained by plotting values of the abovementioned dispersion index value as a mathematical function of the number of spokes per respiratory cycle, while the sequence controlling circuitry 120 performs sampling at a platinum angle PA(N) where N=4, when the data from the exhalation period temporal phase in one respiratory cycle is extracted. As illustrated in FIG. 4B, when N=4 is satisfied, because the dispersion index value exhibits a decreasing tendency in the region where the number of spokes per respiratory cycle is in the range of 16 to 20, N=4 does not yield appropriate sampling in this region.

Figure 4C:
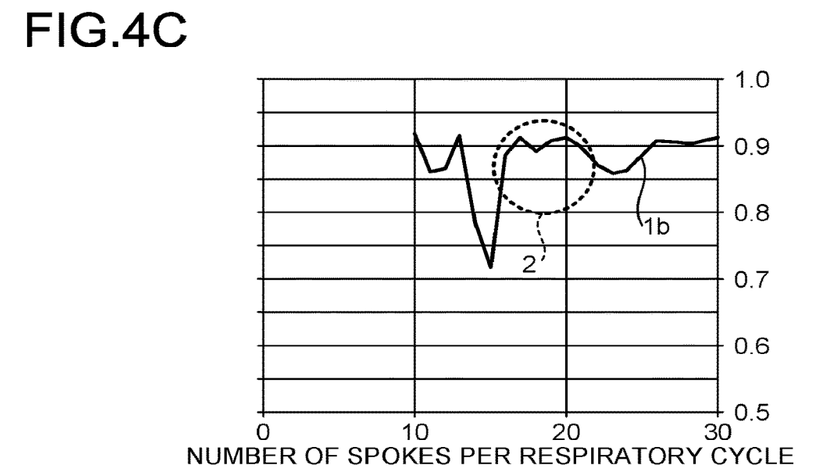
FIG. 4C is another chart for explaining the magnetic resonance imaging method according to the first embodiment.

In contrast, in FIG. 4C, chart 1b is obtained by plotting values of the abovementioned dispersion index value as a mathematical function of the number of spokes per respiratory cycle, while the sequence controlling circuitry 120 performs sampling at a platinum angle PA(N) where N=5, when the data from the exhalation period temporal phase in one respiratory cycle is extracted. As illustrated in FIG. 4C, when N=5 is satisfied, in region 2 where the number of spokes per respiratory cycle is in the range of 16 to 20, the values of the dispersion index value are improved compared to the example of N=4. It is therefore understood that in this region, N=5 yields more desirable sampling than N=4 does. By employing the controlling function 133, the processing circuitry 150 performs the same calculation with respect to various values of N and thus selects N=5 as an optimal acquisition pattern.

In the explanations using FIGS. 4A, 4B, and 4C, the data from the exhalation period temporal phase in one respiratory cycle is used, so that the value of N that maximizes the dispersion index value is used for determining the acquisition pattern. This procedure is based on the assumption that an optimal value of N for exhalation periods can often be optimal also for data from inhalation periods. Accordingly, it is not intended to exclude calculating a value of N separately that is optimal for the data from an inhalation period. It is acceptable to separately calculate an optimal acquisition pattern for the data from an inhalation period.

Subsequently, at step S140, on the basis of the acquisition pattern selected at step S130, the sequence controlling circuitry 120 acquires data in a non-Cartesian coordinate system, by using the plurality of trajectories having the mutually-different rotation angles that were set at step S130 on the basis of the cycle of the biological information. For example, the sequence controlling circuitry 120 acquires the data by executing a pulse sequence of a two-dimensional (2D) radial acquisition, while using the plurality of trajectories having the mutually-different rotation angles that are determined by the platinum angle PA(N) corresponding to the N selected at step S130. In other words, the sequence controlling circuitry 120 acquires k-space data by performing the non-Cartesian sampling, while rotating the trajectory at the rotation angles that were set on the basis of the cycles of the biological information. That is to say, the processing circuitry 150 is configured to set the rotation angles of the k-space trajectories on the basis of the biological information of the subject to be imaged. For instance, the processing circuitry 150 sets the rotation angles of the trajectories, on the basis of the biological information and the quantity of the lines of the trajectories. After that, the processing circuitry 150 obtains the k-space data by rotating the trajectory at the rotation angles having been set.

Subsequently, at step S150, by employing the generating function 136, the processing circuitry 150 generates a magnetic resonance image by arranging the k-space data acquired at step S140 and reconstructing the k-space data.

As explained above, in the first embodiment, by employing the controlling function 133, the processing circuitry 150 is configured to select the optimal acquisition pattern on the basis of the dispersion index value, so that the sequence controlling circuitry 120 performs the radial sampling by using the selected platinum angle. Consequently, in the situation where cyclic movements such as respiration are present while involving individual differences among subjects, for example, it is possible to improve the dispersiveness of the k-space data with respect to each of the subjects and to thus enhance the image quality.

First Modification Example

Figure 5:
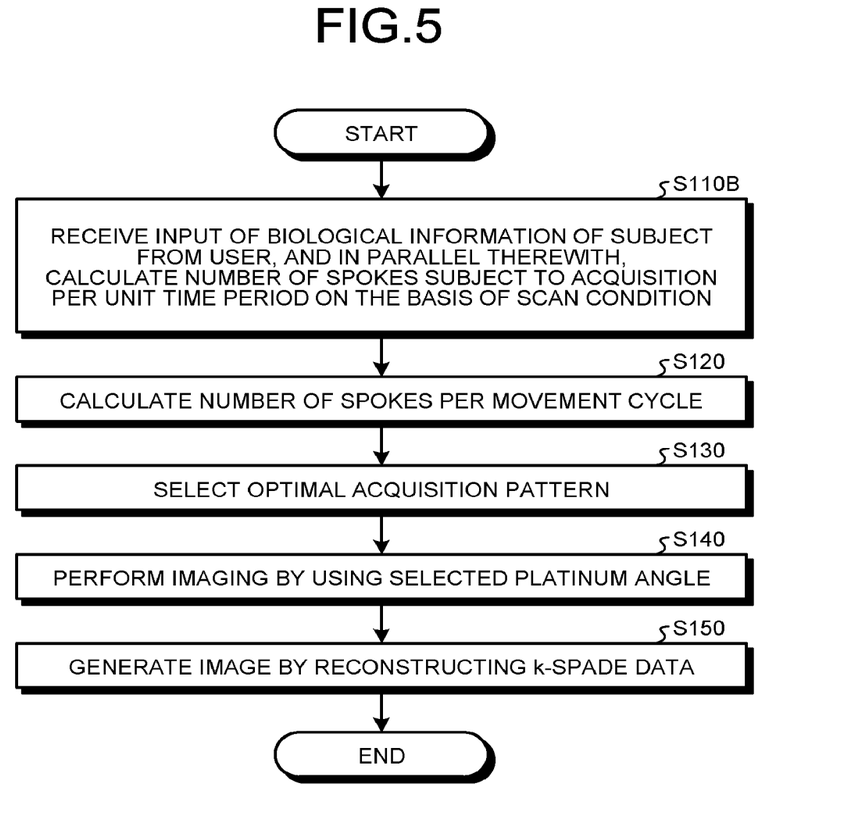
FIG. 5 is a flowchart for explaining a magnetic resonance imaging method according to another embodiment.

In the first embodiment, the example was explained in which, at steps S100 and S110A in FIG. 3, the processing circuitry 150 acquires the biological information of the subject, via a respiratory information acquiring device or an electrocardiograph, for example. However, possible embodiments are not limited to this example. By employing the controlling function 133, the processing circuitry 150 may receive an input of biological information from the user. FIG. 5 presents a flowchart in this example.

According to an embodiment in the first modification example, at step S110B in place of steps S100 and S110A in FIG. 3, by employing the controlling function 133, the processing circuitry 150 receives biological information about respiratory characteristics or the like of the subject from the user via the input device 134 and further calculates the number of spokes subject to the acquisitions per unit time period on the basis of a scan condition. At steps S120 through S150, the same processes as those in the first embodiment are performed.

For example, the controlling function 133 is configured to prompt the user to input a respiratory cycle and receive the input as the biological information. Further, for the biological information, the input device 134 may present the user with qualitative selectable options such as "shallow breathing", "normal", and "deep breathing" so that the user selects one of the options. The controlling function 133 may accordingly receive the respiratory cycle associated with the selected option as the biological information. Although the respiratory cycle is input in the present example, other type of biological information may be received. For instance, when the input device 134 is configured to be able to receive information about heartbeats or a pulse wave, it is possible to receive an input of a heart rate measured in advance or to present selectable options such as "a fast pulse", "normal", and "a slow pulse".

According to the embodiment in the first modification example, it is possible to select an optimal acquisition pattern on the basis of the input by the user, even when a device configured to acquire the biological information such as a respiratory information acquiring device or an electrocardiograph is not attached to the subject. Further, no burden of wearing a biological information acquiring device is imposed on the subject. In addition, the workflow is improved because the procedure of attaching the device to the subject is eliminated.

Second Modification Example

In the first embodiment, at step S130, the controlling function 133 of the processing circuitry 150 is configured to select the optimal acquisition pattern on the basis of the values of the dispersion index value. However, possible embodiments are not limited to this example. At step S130, by employing the controlling function 133, the processing circuitry 150 may select an appropriate acquisition pattern from among a plurality of acquisition patterns, in accordance with an index value related to safety of the subject. In other words, the processing circuitry 150 may select the acquisition pattern from among a plurality of acquisition patterns having mutually-different settings for trajectory rotation angles, in accordance with the index value related to safety of the subject, such as a time change rate dB/dt of the magnetic field.

In an embodiment according to a second modification example, the processing circuitry 150 is configured, by employing the controlling function 133, to select an acquisition pattern on the basis of the time change rate dB/dt of the magnetic field, which is an example of the index value related to safety. For example, the time change rate of a gradient magnetic field increases as the rotation angle of the spokes increases. Accordingly, it is necessary, in some situations, to select an acquisition pattern while taking dB/dt into account. For example, by employing the controlling function 133, the processing circuitry 150 selects an acquisition pattern by which dB/dt is smaller than a threshold value. For example, the threshold value may be the largest dB/dt value defined in a safety standard or may be an arbitrarily set value. Further, in another example, by employing the controlling function 133, the processing circuitry 150 may select such an acquisition pattern that minimizes dB/dt. In yet another example, by employing the controlling function 133, the processing circuitry 150 may select an appropriate acquisition pattern, on the basis of both of values of the dispersion index value and the index value related to safety. In an example, by employing the controlling function 133, the processing circuitry 150 may select, as an appropriate acquisition pattern, such an acquisition patten that has the best dispersion index value among acquisition patterns of each of which the index value related to safety falls within a normal range.

According to the embodiment in the second modification example, it is possible to select the optimal acquisition pattern by using the index value related to safety. Consequently, without the user paying particular attention, it is possible to obtain an image having high image quality within the range compliant with the safety standard required of the MRI apparatus. Further, by determining the acquisition pattern with the use of both the index value related to safety and the dispersion index value, it is possible to further shorten the workflow before determining the optimal acquisition pattern.

Third Modification Example

The optimal acquisition pattern selected at step S130 and the imaging processes performed at step S140 are not limited to those described in the first embodiment. In an embodiment according to a third modification example, a variation of the acquisition pattern will be discussed.

Figure 6A:
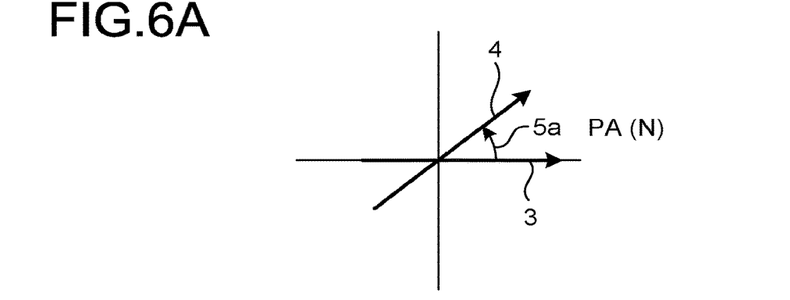
FIG. 6A is a chart for explaining a magnetic resonance imaging method according to yet another embodiment.
Figure 6B:
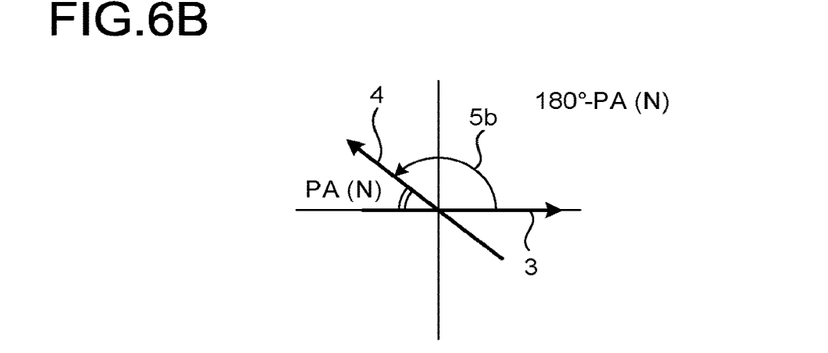
FIG. 6B is a chart for explaining the magnetic resonance imaging method according to said yet another embodiment.
Figure 6C:
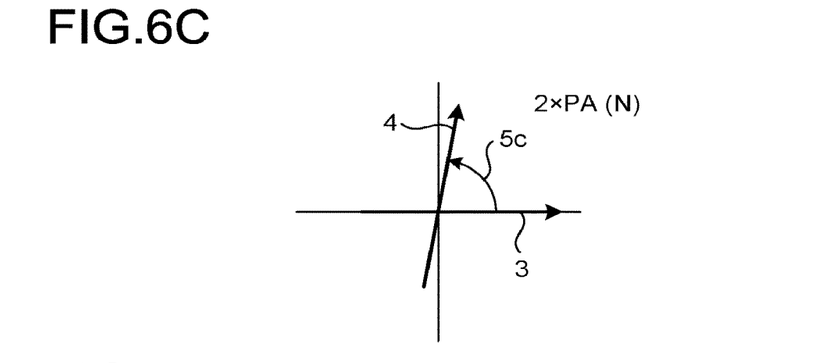
FIG. 6C is a chart for explaining the magnetic resonance imaging method according to said yet another embodiment.
Figure 6D:
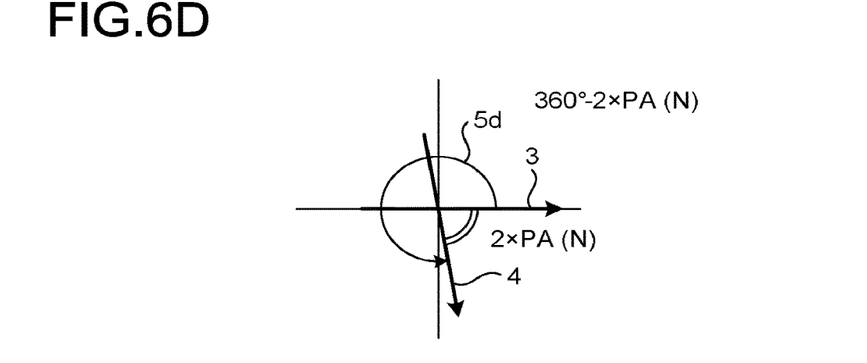
FIG. 6D is a chart for explaining a magnetic resonance imaging method according to said yet another example.

FIGS. 6A to 6D illustrate a variation of the acquisitions using the platinum angle PA(N). FIG. 6A illustrates a basic pattern in which the rotation angle 5a between a spoke 3 of a k-th acquisition and another spoke 4 of a (k+1)th acquisition is equal to platinum angle PA(N). In contrast, FIGS. 6B to 6D illustrate examples extended from the basic pattern in FIG. 6A. FIG. 6B illustrates a pattern in which the rotation angle 5b between the spoke 3 of the k-th acquisition and the spoke 4 of the (k+1)th acquisition is equal to 180°−PA(N). FIG. 6C illustrates a pattern in which the rotation angle 5c between the spoke 3 of the k-th acquisition and the spoke 4 of the (k+1)th acquisition is equal to 2×PA(N). FIG. 6D illustrates a pattern in which the rotation angle 5d between the spoke 3 of the k-th acquisition and the spoke 4 of the (k+1)th acquisition is equal to 360°−2×PA(N).

Instead of the platinum angle PA(N) itself, the sequence controlling circuitry 120 may perform the acquisitions by using a pseudo platinum angle, which is an angle approximate to the platinum angle PA(N). In this situation, the pseudo platinum angle is configured to be, for example, an angle of a rational number that is close to the platinum angle and of which the numerator and the denominator is each a relatively small integer. In another example, the sequence controlling circuitry 120 may sort the n spokes each rotated at the platinum rotation angle according to the magnitudes of the angles formed with an initial line serving as a reference, so as to execute an acquisition sequence, with respect to the spokes re-arranged at regular intervals in such a manner that the angle formed by an i-th spoke is equal to 360°×(i/n).

Further, there are other variations of the optimal acquisition pattern selected at step S130 and the imaging processes performed at step S140.

For example, at step S140, the sequence controlling circuitry 120 may execute an acquisition sequence by simple division into N sections, i.e., by using spokes of which the angle of an i-th spoke is equal to 360°×(i/N). In that situation, at step S130, by employing the controlling function 133, the processing circuitry 150 calculates a dispersion index value with respect to each value of N and further selects an optimal acquisition pattern on the basis of the calculated dispersion index values.

In another example, at step S140, the sequence controlling circuitry 120 may execute an acquisition sequence with division by N/M cycles, i.e., by using spokes of which the angle of an i-th spoke is equal to 360°×(i/N*M). In that situation, at step S130, by employing the controlling function 133, the processing circuitry 150 calculates a dispersion index value with respect to each value of N and M and further selects an optimal acquisition pattern on the basis of the calculated dispersion index values.

Figure 7:
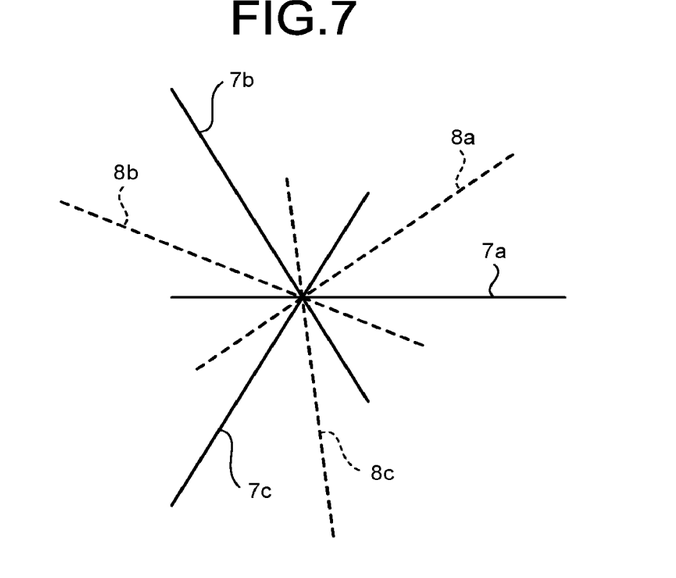
FIG. 7 is a drawing for explaining a magnetic resonance imaging method according to another modification example.

In yet another example, at step S140, the sequence controlling circuitry 120 may execute the acquisition sequence by using a grouped golden angle, i.e., using a sequence by which a plurality of acquisitions in a set are each performed while varying the angle by the golden angle. In other words, the plurality of acquisitions in the one set are performed by executing an acquisition sequence by which each acquisition is performed while varying the angle by the golden angle. That is to say, the processing circuitry 150 is configured to generate sequence information by which the plurality of acquisitions in the one set are each performed while varying the angle by the golden angle. FIG. 7 illustrates an example of the grouped golden angle where three spokes are in one set. In FIG. 7, the spokes 7a, 7b, and 7c and the spokes 8a, 8b, and 8c arranged at 120-degree Intervals each correspond to one set of acquisitions. For example, the angle between the spoke 7a and the spoke 8a is the golden angle. For example, the sequence controlling circuitry 120 performs one set of acquisitions on the spokes 7a, 7b, and 7c and subsequently performs another set of acquisitions on the spokes 8a, 8b, and 8c. At step S130, in the acquisitions using the grouped golden angle while n spokes are included in one set, the processing circuitry 150 calculates, by employing the controlling function 133, a dispersion index value for each value of n and further selects an optimal acquisition pattern on the basis of the calculated dispersion index values.

In yet another example, at step S140, the sequence controlling circuitry 120 may execute an acquisition sequence by using a bit reversed order. In other words, k-space data is acquired by executing a BitReverseOrder acquisition sequence. That is to say, the processing circuitry 150 is configured to generate sequence information by which k-space data is acquired by using BitReverseOrder. In this situation, for example, the acquisition sequence using the bit reversed order characterized by a set of natural numbers (N, M, L) where N, M, and L are each a natural number denotes an acquisition sequence following a specific order by which, at the first step, acquisitions are sequentially performed on N spokes obtained by dividing one round into N sections; at the second step, of the spokes obtained by dividing the one round into N×M sections, acquisitions are sequentially performed on such spokes that were not subject to the acquisitions at the first step; and at the third step, of the spokes obtained by dividing one round into N×M×L sections, acquisitions are sequentially performed on such spokes that were not subject to the acquisitions at the first and the second steps. At step S130, by employing the controlling function 133, the processing circuitry 150 calculates a dispersion index value by varying a parameter characterizing the acquisition sequence using the bit reversed order and further selects an optimal acquisition pattern on the basis of the calculated dispersion index values.

In yet another example of the process at step S130, by employing the controlling function 133, the processing circuitry 150 may calculate a dispersion index value for the golden angle and for each of the variations thereof, so as to select an optimal acquisition pattern on the basis of the calculated dispersion index values. For example, by employing the controlling function 133, the processing circuitry 150 may calculate a dispersion index value for each of the pulse sequences corresponding to rotation angles of the golden angle GA and variations thereof such as 180°−GA, 2×GA, and 360°−2×GA and may further select an optimal variation on the basis of the calculated dispersion index values.

Further, in the embodiment, the example was explained in which the sequence controlling circuitry 120 performs the 2D radial acquisition; however, possible embodiments are not limited to the 2D radial acquisition. The present disclosure is applicable to various types of acquisition sequences by which acquisitions are performed in a non-Cartesian coordinate system while varying the encoding direction in predetermined cycles, e.g., 2D-based acquisition sequences such as a 2D spiral acquisition and three-dimensional (3D)-based acquisition sequences such as a Stack of Stars acquisition, and a Koosh Ball acquisition or a cone trajectory acquisition used in Ultrashort TE (UTE) imaging or the like. Further, the present disclosure is also applicable to 2D-based acquisition sequences such as JET or Periodically Rotated Overlapping Parallel Lines with enhanced reconstruction (PROPELLER) by which an acquisition is performed while rotating a blade defined as a belt-shaped region structured with a plurality of parallel trajectories. In other words, possible embodiments of the present disclosure are not limited to the situations where the rotation angle is changed every time an acquisition is performed on one spoke.

According to the embodiment in the third modification example, it is possible to set the acquisition pattern in which the rotation angles using the golden angle and the platinum angle are extended. It is therefore possible to flexibly address various types of imaging sequences. Further, it is also possible to select an optimal pattern from among a certain number of publicly-known acquisition patterns that use the golden angle, by using the biological information of the subject and the scan condition. It is therefore possible to enhance image quality of certain imaging methods using publicly-known techniques.

Reconstructing Methods and Imaging Methods

The configuration according to the first embodiment may be carried out together with any of various types of image reconstruction algorithms such as Compressed Sensing (CS) or dynamic imaging. In other words, the processing circuitry 150 may be configured to generate an image by reconstructing the k-space data while using compressed sensing or the like.

Depending on the image reconstruction algorithm being used (e.g., compression sensing), the aforementioned dispersion index value may not be suitable as an image quality evaluation index, in some situations. In those situations, it is also acceptable to set another index value adaptive to the reconstruction algorithm and to further select an optimal acquisition pattern on the basis of the index value.

In the optimal acquisition pattern selected at step S130, because the increasing rate of angles per unit time period is constant, the dispersiveness of the k-space data is excellent no matter at which time a section of data is extracted. Accordingly, this configuration is suitable for situations where data obtained by a radial scan is divided into a plurality of frames so as to be reconstructed as separate images, like in dynamic reconstruction schemes. In other words, when a radial coordinate system is selected as the non-Cartesian coordinate system, the processing circuitry 150 may dynamically generate an image by employing the generating function 136 to perform a reconstruction process while using a part of the k-space data acquired from the radial coordinate system.

Second Embodiment

In the first embodiment, at step S130, by employing the controlling function 133, the processing circuitry 150 selects the optimal acquisition pattern on the basis of the values of the dispersion index value. However, possible embodiments are not limited to this example. By employing the controlling function 133, the processing circuitry 150 may optimize the pulse sequence to be executed at step S140.

In other words, in a second embodiment, the processing circuitry 150 is configured, by employing the controlling function 133, to optimize the pulse sequence to be executed at step S140, so that a parameter such as Repetition Time (TR) and/or Echo Time (TE) becomes optimal, while the value of N used as the platinum angle PA(N) is fixed.

Figure 8:
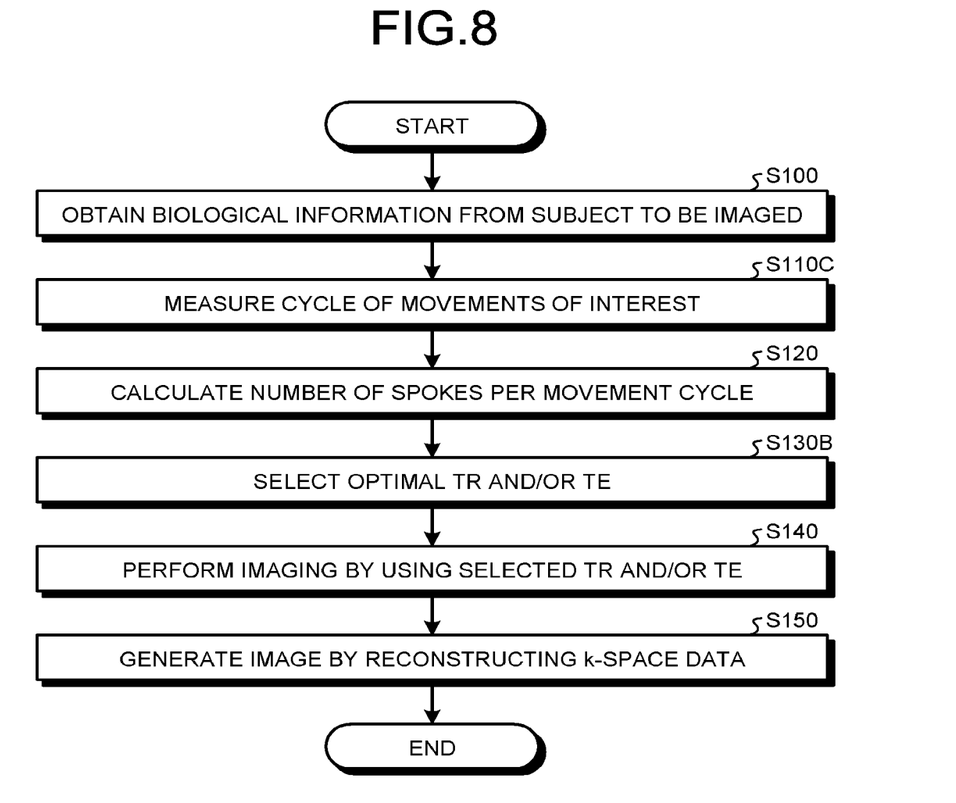
FIG. 8 is a flowchart illustrating a processing procedure performed by a magnetic resonance imaging apparatus according to a second embodiment.

An example of this process is illustrated in FIG. 8.

Similar to the first embodiment, at step S100, by employing the controlling function 133, the processing circuitry 150 obtains biological information such as information about respiration or information about heartbeats, from the subject to be imaged. Subsequently, at step S110C, the processing circuitry 150 measures the cycle of the movements of interest by employing the controlling function 133. After that, at step S120, by employing the controlling function 133, the processing circuitry 150 calculates the number of spokes per movement cycle.

Subsequently, at step S130B, by employing the controlling function 133, the processing circuitry 150 varies the parameter of the pulse sequence to be executed, on the basis of values of the dispersion index value or the like to optimize the pulse sequence to be executed at step S140. For example, prior to acquiring the k-space data by using a plurality of trajectories having mutually-different rotation angles at step S140, the processing circuitry 150 adjusts, by employing the controlling function 133, the parameter of the acquisition sequence for the k-space data such as Repetition Time (TR) and/or Echo Time (TE), on the basis of a parameter determining the rotation angles, the cycle of the biological information measured at step S110A, and the value of the dispersion index value calculated for each of the parameters of the acquisition sequence for the k-space data to be executed at step S140. In other words, prior to obtaining the k-space data by rotating the trajectory at the rotation angles being set, the processing circuitry 150 adjusts the sequence information such as TR and/or TE to be used for acquiring the k-space data, in accordance with the distribution of the k-space data. In one example, by employing the controlling function 133, the processing circuitry 150 calculates such a value of TR and/or TE that makes the calculated value of the index dispersion value most desirable, as the parameter of the acquisition sequence to be executed at step S140. In this manner, because the dispersion index value is calculated for each of the parameters of the acquisition sequence, the sequence controlling circuitry 120 is able to calculate the parameter of the acquisition sequence that causes the number of spokes per movement cycle to have an appropriate value.

Further, by employing the controlling function 133, the processing circuitry 150 may present the user via the display 135 with adjustment candidate values for the parameter of the acquisition sequence for the k-space data. In other words, prior to obtaining the k-space data by rotating the trajectory at the rotation angles being set, the processing circuitry 150 may present the candidate values to adjust the sequence information such as TR and/or TE used for acquiring the k-space data, in accordance with the distribution of the k-space data.

After that, at step S140, the sequence controlling circuitry 120 acquires data by executing the pulse sequence in a non-Cartesian coordinate system, on the basis of the optimal TR and/or TE selected at step S130.

After that, at step S150, by employing the generating function 136, the processing circuitry 150 generates a magnetic resonance image by arranging the k-space data acquired as step S140 and reconstructing the k-space data.

As explained above, according to the second embodiment, it is possible to optimize the pulse sequence to be executed when cyclic movements such as respiration are present, for example. It is therefore possible to enhance the image quality.

Computer Programs

It is possible to execute the instructions in the processing procedures described in the above embodiments, on the basis of a computer program (hereinafter, "program") realized with software. As a result of a generic computer storing the program therein in advance and reading the program, it is also possible to achieve the same advantageous effects as those achieved by the magnetic resonance imaging apparatus 100 according to the above embodiments. The instructions described in the above embodiments may be recorded as a computer-executable program in a magnetic disk (e.g., a flexible disk, a hard disk), an optical disk (e.g., a Compact Disk Read-Only Memory [CD-ROM], a Compact Disk Recordable [CD-R], a Compact Disk Rewritable [CD-RW], a Digital Versatile Disk Read-Only Memory [DVD-ROM], a DVD±Recordable [DVD±R], a DVD±Rewritable [DVD±RW]), a semiconductor memory, or a similar recording medium. As long as the storage medium is readable by a computer or an embedded system, it is possible to use any storage format. By reading the program from the recording medium and causing a CPU to execute the instructions written in the program on the basis of the program, the computer is able to realize the same operations as those performed by the magnetic resonance imaging apparatus 100 according to the above embodiments. Further, when obtaining or reading the program, the computer may obtain or read the program via a network.

Further, on the basis of the instructions of the program installed from the storage medium into the computer or the embedded system, an Operating System (OS) working in the computer or middleware (MW) such as database management software of a network may execute a part of the processes performed for realizing the embodiments described above. Further, the storage medium does not necessarily have to be a medium independent of the computer or the embedded system. Examples of the storage medium include a storage medium that downloads the program transferred via a Local Area Network (LAN) or the internet and that stores or temporarily stores therein the transferred program. Further, the number of storage media does not necessarily have to be one. Examples of the storage medium according to the embodiments include the situation where the processes according to the embodiments are executed from two or more media. It is possible to use any configuration for the medium (media).

The computer or the embedded system according to the embodiments is configured to execute the processes in the above embodiment on the basis of the program stored in the one or more storage media and may be configured as a single apparatus such as a personal computer or a microcomputer or as a system in which a plurality of apparatuses are connected together via a network. Further, the "computer" according to the embodiments does not necessarily have to be a personal computer and may be an arithmetic processing device included in an information processing device or a microcomputer. The term "computer" is a generic name for any device or apparatus capable of realizing the functions of the embodiments by using the program.

According to at least one aspect of the embodiments described above, it is possible to enhance the image quality.

With respect to the embodiments described above, the following additional notes are disclosed as some and optional features of the invention.

(Additional notes)

A magnetic resonance imaging apparatus according to at least one aspect of the present disclosure includes processing circuitry. The processing circuitry is configured to set a rotation angle of a non-Cartesian trajectory in a k-space on the basis of information related to cyclic movements of a subject to be imaged (or biological information), to obtain k-space data by rotating the non-Cartesian trajectory at the set rotation angle, and to generate an image by reconstructing the k-space data.

The biological information may be information about respiration.

The biological information may be information about heartbeats.

The processing circuitry may set the rotation angle of the trajectory on the basis of the information related to the cyclic movements and information related to the quantity of lines of the trajectory.

The processing circuitry may select, at k-space data acquired at time points determined based on the information related to the cyclic movements, an acquisition pattern in accordance with a distribution of the k-space data to be used to generate the image, from among a plurality of acquisition patterns having mutually-different settings for the rotation angle of the trajectory.

The processing circuitry may select an acquisition pattern having high dispersiveness of the k-space, from among the plurality of acquisition patterns.

The plurality of acquisition patterns may have mutually-different rotation angles. The processing circuitry may calculate an index representing dispersiveness corresponding to each rotation angle and select a rotation angle of a trajectory having highest dispersiveness as acquisition pattern used for imaging.

The biological information may be obtained from a biological information obtaining device.

The biological information may be obtained through an input by a user.

The processing circuitry may select an acquisition pattern in accordance with an index value related to safety of the subject, from among a plurality of acquisition patterns having mutually-different settings for the rotation angle of the trajectory.

The index value related to safety may be dB/dt. Prior to obtaining the k-space data by rotating the trajectory at the set rotation angle, the processing circuitry may adjust sequence information used for acquiring the k-space data in accordance with a distribution of the k-space data.

Prior to acquiring the k-space data by using the trajectory, the processing circuitry may present a candidate value for adjusting sequence information used for acquiring the k-space data in accordance with a distribution of the k-space data.

Prior to acquiring the k-space data by using the trajectory, the processing circuitry may adjust a parameter of an acquisition sequence for the k-space data on the basis of a parameter determining the rotation angle and a cycle of the biological information.

Prior to acquiring the k-space data by using the trajectory, processing circuitry may present an adjustment candidate value for a parameter of an acquisition sequence for the k-space data on the basis of a parameter determining the rotation angle and a cycle of the biological information.

The sequence information may include one or both of Repetition Time (TR) and Echo Time (TE).

In the plurality of acquisition patterns, the rotation angle may be expressed as $180°/(N+1/\psi)$, where N is a natural number, and $\psi=1.618$.

The processing circuitry may generate sequence information by which a plurality of acquisitions in a set are each performed while varying an angle by a golden angle.

The processing circuitry may generate sequence information by which the k-space data is acquired by using BitReverseOrder.

The processing circuitry may generate the image by reconstructing the k-space data while using compressed sensing.

The k-space may be a radial coordinate system. The processing circuitry may dynamically generate the image through the reconstruction by using a part of the k-space data acquired in the radial coordinate system.

The information related to the quantity of lines of trajectory may be quantity of lines of trajectory acquired per unit time.

The time points determined based on the biological information may be expiratory phase.

A magnetic resonance imaging method according to at least one aspect of the present disclosure includes:

setting a rotation angle of a non-Cartesian trajectory in a k-space on the basis of information related to cyclic movements of a subject to be imaged;

obtaining k-space data by rotating the trajectory at the set rotation angle; and generating an image by reconstructing the k-space data.

A method according to at least one aspect of the present disclosure includes: obtaining information related to cyclic movements from a subject to be imaged; and generating an image by arranging, in a non-Cartesian coordinate system, k-space data acquired by using a plurality of trajectories being set on the basis of a cycle of the biological information and having mutually-different rotation angles and reconstructing the k-space data.

Prior to the acquisition the k-space data by using the plurality of trajectories, a parameter of an acquisition sequence for the k-space data may be adjusted on the basis of a parameter determining the rotation angle and a cycle of the biological information.

Prior to the acquisition the k-space data by using the plurality of trajectories, an adjustment candidate value for a parameter of an acquisition sequence for the k-space data may be presented, on the basis of a parameter determining the rotation angle and a cycle of the biological information.

A magnetic resonance imaging apparatus according to at least one aspect of the present disclosure includes processing circuitry configured:

to obtain biological information from a subject to be imaged; and to generate an image by arranging, in a non-Cartesian coordinate system, k-space data acquired by using a plurality of trajectories being set on the basis of a cycle of the biological information and having mutually-different rotation angles and reconstructing the k-space data.

In a further aspect, a magnetic resonance imaging apparatus is provided comprising processing circuitry (150) configured:

to receive an input of temporal data of cyclic movements of a subject to be imaged;

to set a rotation angle of a non-Cartesian trajectory in a k-space on the basis of the received temporal data;

to obtain k-space data by rotating the non-Cartesian trajectory at the set rotation angle; and to generate an image by reconstructing the k-space data.

In an embodiment, the processing circuitry is configured to obtain k-space data using a non-Cartesian-type acquisition sequence, in which acquisitions are performed using a plurality of non-Cartesian trajectories going through the origin of k-space, the non-Cartesian trajectories being rotated from one another using the set rotation angle.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. A magnetic resonance imaging apparatus comprising processing circuitry configured:
   to set a rotation angle of a non-Cartesian trajectory in a k-space on a basis of information related to cyclic movements of a subject to be imaged;
   to obtain k-space data by rotating the non-Cartesian trajectory at the set rotation angle;
   to generate an image by reconstructing the k-space data;
   to calculate a quantity of lines of trajectory acquired at one cycle of the cyclic movements; and
   to select, for k-space data acquired the one cycle of the cyclic movements, an acquisition pattern, from among a plurality of acquisition patterns, by evaluating a distribution of the k-space data to be used to generate the image, for a plurality of quantities of lines of trajectory in a range having the calculated quantity as a center.

2. The magnetic resonance imaging apparatus according to claim 1, wherein the cyclic movements are due to respiration.

3. The magnetic resonance imaging apparatus according to claim 1, wherein the processing circuitry sets the rotation angle of the trajectory on a basis of the information related to the cyclic movements and information related to a quantity of lines of the trajectory.

4. The magnetic resonance imaging apparatus according to claim 3, wherein the information related to the quantity of lines of trajectory is a quantity of lines of trajectory acquired per unit time.

5. The magnetic resonance imaging apparatus according to claim 1, wherein the processing circuitry selects an acquisition pattern having highest dispersiveness of the k-space, from among the plurality of acquisition patterns.

6. The magnetic resonance imaging apparatus according to claim 1, wherein the information related to the cyclic movements are obtained through an input by a user.

7. The magnetic resonance imaging apparatus according to claim 1, wherein the processing circuitry selects an acquisition pattern in accordance with an index value related to safety of the subject, from among a plurality of acquisition patterns having mutually-different settings for the rotation angle of the trajectory.

8. The magnetic resonance imaging apparatus according to claim 1, wherein, prior to obtaining the k-space data by rotating the trajectory at the set rotation angle, the processing circuitry adjusts sequence information used for acquiring the k-space data in accordance with a distribution of the k-space data.

9. The magnetic resonance imaging apparatus according to claim 8, wherein the sequence information includes one or both of Repetition Time (TR) and Echo Time (TE).

10. The magnetic resonance imaging apparatus according to claim 1, wherein, prior to acquiring the k-space data by using the trajectory, the processing circuitry presents a candidate value for adjusting sequence information used for acquiring the k-space data in accordance with a distribution of the k-space data.

11. The magnetic resonance imaging apparatus according to claim 1, wherein the processing circuitry generates sequence information by which a plurality of acquisitions in a set are each performed while varying an angle by a golden angle.

12. The magnetic resonance imaging apparatus according to claim 1, wherein
   the k-space is a radial coordinate system, and
   the image is dynamically generated through the reconstruction by using a part of the k-space data acquired in the radial coordinate system.

13. The magnetic resonance imaging apparatus according to claim 1, wherein time points determined based on the information related to the cyclic movements is an expiratory phase.

14. A magnetic resonance imaging method comprising:
   setting a rotation angle of a non-Cartesian trajectory in a k-space on a basis of information related to cyclic movements of a subject to be imaged;
   obtaining k-space data by rotating the trajectory at the set rotation angle; and
   generating an image by reconstructing the k-space data;
   calculating a quantity of lines of trajectory acquired at one cycle of the cyclic movements; and
   selecting, for k-space data acquired the one cycle of the cyclic movements, an acquisition pattern, from among a plurality of acquisition patterns, by evaluating a distribution of the k-space data to be used to generate the image, for a plurality of quantities of lines of trajectory in a range having the calculated quantity as a center.

* * * * *